US009615607B2

(12) United States Patent
Liu (10) Patent No.: US 9,615,607 B2
(45) Date of Patent: Apr. 11, 2017

(54) ELECTRONIC CIGARETTE (71) Applicant: Qiuming Liu, Guangdong (CN)

(72) Inventor: Qiuming Liu, Guangdong (CN)

(73) Assignee: HUIZHOU KIMREE TECHNOLOGY CO., LTD. SHENZHEN BRANCH, Shenzhen (CN)

( * ) Notice: Subject to any disclaimer, the term of this patent is extended or adjusted under 35 U.S.C. 154(b) by 736 days.

(21) Appl. No.: 14/096,897

(22) Filed: Dec. 4, 2013

(65) Prior Publication Data
US 2015/0027467 A1 Jan. 29, 2015

(30) Foreign Application Priority Data

Jul. 24, 2013 (CN) ...................... 2013 2 0444321 U (51) Int. Cl.
*A24F 47/00* (2006.01)
*A61M 15/06* (2006.01)

(52) U.S. Cl.
CPC ........... *A24F 47/008* (2013.01); *A61M 15/06* (2013.01)

(58) Field of Classification Search
CPC ...... A24F 47/00; A24F 47/002; A24F 47/004; A24F 47/008; A61M 15/06
See application file for complete search history.

(56) References Cited

U.S. PATENT DOCUMENTS

| 5,894,841 A * | 4/1999 | Voges | A24F 47/008 128/200.14 |
| 2010/0319686 A1* | 12/2010 | Schennum | A24F 47/002 128/200.23 |
| 2014/0261493 A1* | 9/2014 | Smith | A24F 47/008 131/328 |
| 2014/0373833 A1* | 12/2014 | Liu | A61M 11/042 128/202.21 |
| 2015/0020827 A1* | 1/2015 | Liu | A24F 47/008 131/329 |

(Continued)

OTHER PUBLICATIONS

Gaffer et al., Why are we still using 510 connectors??[downloaded online Sep. 26, 2016], Mar. 2, 2013, downloaded from www.thevapersden.com.*

(Continued)

*Primary Examiner* — Anthony Calandra
(74) *Attorney, Agent, or Firm* — Tim Tingkang Xia, Esq.; Locke Lord LLP (57) ABSTRACT

The present application discloses an electronic cigarette, which comprises a battery rod, an atomizer, and a connection structure; the connection structure includes a first connecting piece and a second connecting piece; a buckle is deposited on an exterior sidewall of the first connecting piece; a receiving hollow, a guiding slot and a stop slot are defined in the second connecting piece; the second connecting piece includes a lower electrode which elastically abuts against the first connecting piece; when assembling the electronic cigarette, inserting the first connecting piece into the receiving hollow and moving downward along the guiding slot; having the first connecting piece press down the lower electrode, which makes the buckle reaches the stop slot, then rotating the first connecting piece so that the buckle enters into the stop slot and is locked.

2 Claims, 6 Drawing Sheets

(56) References Cited

U.S. PATENT DOCUMENTS

2015/0272221 A1* 10/2015 Liu ...................... A24F 47/008
                                                          131/273

OTHER PUBLICATIONS

Blickblocks et al., Threaded mounts are inferior. When will we see a standardized bayonet mount? [downloaded on Sep. 26, 2016],Aug. 19, 2014, downloaded from reddit.com.*
Nicowolf et al., WooHoo! Alternative Connector for 510 [downloaded Sep. 26, 2016], Jul. 11, 2009, downloaded from e-cigarette-forum.com.*

* cited by examiner

ELECTRONIC CIGARETTE

CROSS-REFERENCE TO RELATED APPLICATIONS

This non-provisional application claims priority under 35 U.S.C. §119(a) on Patent Application No. 201320444321.1, filed in P.R. China on Jul. 24, 2013, the entire contents of which are hereby incorporated by reference.

TECHNICAL FIELD

The present application relates to the technical field of cigarette substitute, and more particularly, relates to an electronic cigarette.

BACKGROUND

An electronic cigarette generally includes an atomizer and a battery rod. In the prior art, most of the connections between the atomizers and the battery rods are threaded connections in the electronic cigarettes, and the physical connection and the electrical connection between the atomizer and the battery rod are achieved by rotating the atomizer or the battery rod. After the tobacco tar within the atomizer runs out, by rotating the atomizer in reverse, the atomizer can be taken out and a new atomizer can be replaced.

However, when using the threaded connection, it is not easy to determine whether the connection is in place, the misplacement is prone to occur, the assembly and disassembly are inconvenient, impersonal and the user experience is poor; thereby, when using the electronic cigarette with this kind of connection, user will usually generate a psychological resistance, which is bad for smoking cessation. Additionally, since the appearance and the handle of the electronic cigarette are required to imitate the real cigarette to the limit, and the electronic cigarette itself includes many parts, therefore, the diameter of the electronic cigarette is small, and the wall is relatively thin. However, when defining the thread in the electronic cigarette, it is not only inconvenient for the manufacture of the electronic cigarette, but also the mechanical strength of the electronic cigarette is reduced, which make the electronic cigarette easier to break, and the service life of the electronic cigarette is short.

BRIEF SUMMARY

The objective of the present application is to provide an electronic cigarette with more convenient and more simple assembly, aiming at the drawbacks that the connection between the above-mentioned battery rod and the atomizer is complicate and difficult for alignment in the prior art.

In accordance with one aspect of the present application, there is provided an electronic cigarette, comprising a battery rod, an atomizer, and a connection structure provided on the junction between the battery rod and the atomizer; wherein the connection structure includes a first connecting piece and a second connecting piece, a buckle projects radially from an exterior sidewall of the first connecting piece; a receiving hollow, a guiding slot and a stop slot are defined in the second connecting piece; the receiving hollow is configured to hold the first connecting piece inserted; the guiding slot matching with the buckle is formed on an inner wall of the receiving hollow; the stop slot is in communication with the guiding slot; the second connecting piece includes a lower electrode which elastically abuts against the first connecting piece; when assembling the electronic cigarette, inserting the first connecting piece into the receiving hollow and moving it downward along the guiding slot until the buckle reaches the stop slot, and having the first connecting piece press down the lower electrode, then rotating the first connecting piece so that the buckle enters into the stop slot and is locked.

In one embodiment, the second connecting piece includes an elastomer which is configured to make the lower electrode elastically abut against the first connecting piece. Advantageously, the elastomer is a spring or an elastic insulating part. And an airflow channel is defined in the first connecting piece and/or the second connecting piece, and the airflow channel passes through both ends of the first connecting piece and/or the second connecting piece.

In this embodiment, the first connecting piece includes an upper electrode, and the upper electrode abuts against the lower electrode. The first connecting piece further includes a first insulating part and a first external electrode, the first insulating part and the first external electrode are successively sleeved on an exterior sidewall of the upper electrode; and the first insulating part is configured to make the first external electrode electrically insulated from the upper electrode. The first external electrode includes a main body and an extension portion; the main body is deposited in the atomizer, and the extension portion extends in the direction away from the atomizer; the buckle is deposited on a circumferential exterior sidewall of the extension portion. The second connecting piece further includes a second insulating part and a second external electrode, the second insulating part and the second external electrode are successively sleeved on an exterior sidewall of the lower electrode; and the second insulating part is configured to make the second external electrode electrically insulated from the lower electrode. And the second external electrode is substantially in form of a hollow cylinder, the receiving hollow for containing the first connecting piece is defined on one portion of the second external electrode, and the portion is close to the atomizer; the inner wall of the receiving hollow axially defines the guiding slot for the buckle passing through. A ring-shaped projection is deposited at a circumference of an inner wall of the second external electrode, and one end of the lower electrode passes through the ring-shaped projection, the end is close to the guiding slot.

Yet in this embodiment, a stop slot communicating with the guiding slot is circumferentially defined at an end portion of the inner wall of the receiving hollow and is between the ring-shaped projection and an end of the guiding slot, the end of the guiding slot communicates with the stop slot, and the end wall of the guiding slot and a top wall of the ring-shaped projection form two sidewalls of the stop slot configured for the rotation of the buckle.

Advantageously, the buckle is deposited at an edge portion of the circumferential exterior sidewall of the extension portion. In this case, the lower electrode includes a hollow cylinder, and a coaxial annular bulge is deposited on an exterior sidewall of the hollow cylinder; the coaxial annular bulge abuts against a bottom wall of the ring-shaped projection through the second insulating part at one side of the coaxial annular bulge, and a through hole of the hollow cylinder of the lower electrode forms an airflow channel. And the elastomer is winded up on the hollow cylinder portion at another side of the coaxial annular bulge; when the upper electrode abuts against the lower electrode and presses down the lower electrode, the elastomer shrinks elastically to make the buckle enter into the stop slot.

In another embodiment, the buckle is positioned in a middle portion of the circumferential exterior sidewall of the extension portion. In this case, a flange is provided on one end of the lower electrode, the flange abuts against the top wall of the ring-shaped projection through the second insulating part. Advantageously, the second insulating part is the elastomer. In this case, the second insulating part is made from soft material; when the upper electrode abuts against the lower electrode and presses down the lower electrode, the second insulating part is compressed elastically, which makes the buckle enter into the stop slot.

Preferably, the soft material is at least one kind from polyurethane rubber, silicone rubber and polystyrene.

In according with one aspect of the present application, the atomizer and the battery rod are respectively sleeved with an atomizer sleeve and a battery sleeve; the first connecting piece or the second connecting piece are respectively deposited on the atomizer sleeve and the battery sleeve, and by the connection between the first connecting piece and the second connecting piece, the battery sleeve can be detachably connected to the atomizer sleeve.

When implementing the electronic cigarette of the present application, the following advantageous can be achieved: by mounting the buckle on the first connecting piece, firstly the first connecting piece is inserted into the receiving hollow and makes the buckle move downward along the guiding slot; when the buckle moves to the end of the guiding slot, and the lower electrode is pressed down, then the buckle is rotated, which makes the buckle enter into the stop slot and is locked, so the first connecting piece is connected to the second connecting piece; and when the buckle is limited in the stop slot, the upper electrode elastically abuts against the lower electrode, preventing the buckle from slipping out of the stop slot, and the problem of the atomizer falling off from the inside of the battery rod is avoid. Additionally, the electrical connection in the present application is relatively well, and the mechanical strength is high, which make it not easy to break. Only one buckle is provided, and the construction is simple; it is convenient for the manufacture and it is cost-effective; the assembly method is more convenient and simple. Besides, the battery rod is easier to align with the atomizer, and the user experience is improved.

BRIEF DESCRIPTION OF THE DRAWINGS

The present application will be further described with reference to the accompanying drawings and embodiments in the following, in the accompanying drawings.

DETAILED DESCRIPTION OF THE PREFERRED EMBODIMENT

In order to make the technical features, the propose and the technical effect of the present application more clearly, the present application will now be described in detail with reference to the accompanying drawings and embodiments.

Figure 1:
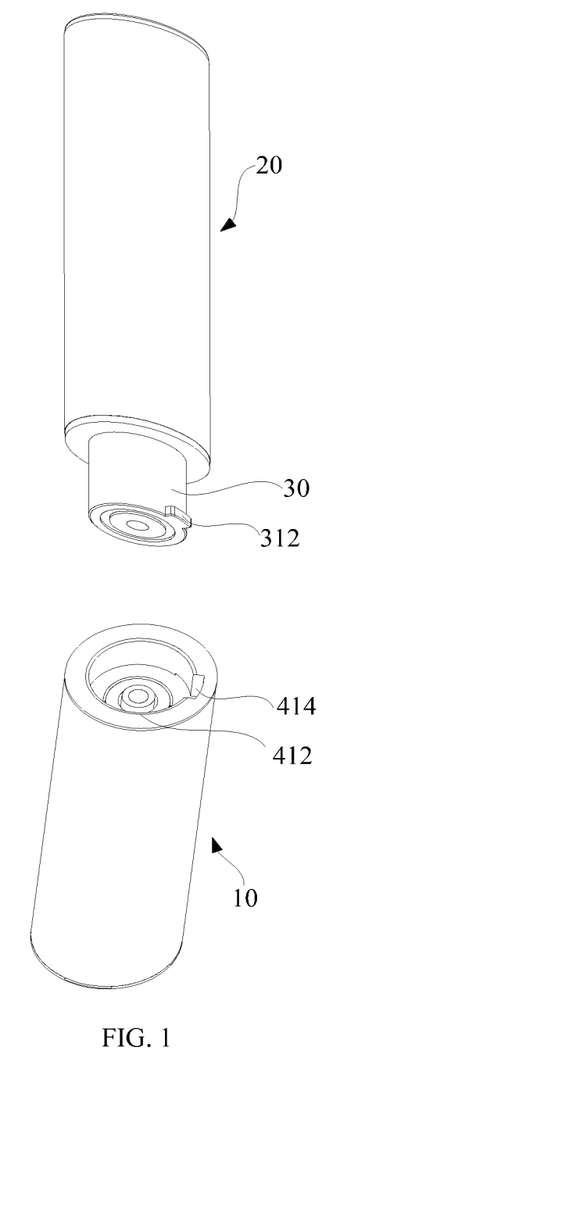
FIG. 1 illustrates a schematic view of an electronic cigarette before assembling according to a first embodiment of the present application.
Figure 2:
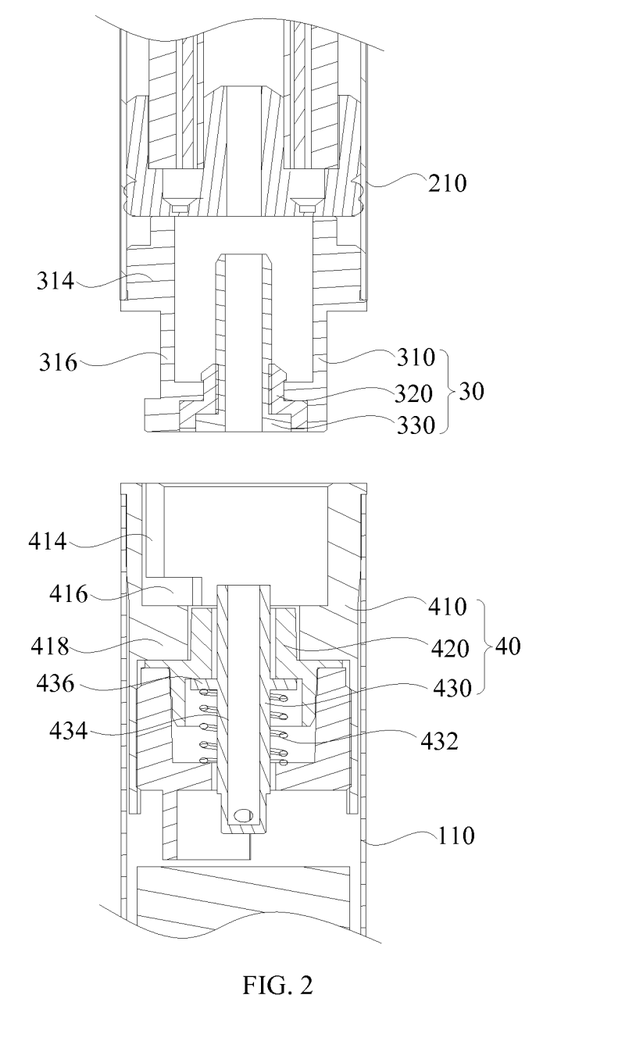
FIG. 2 illustrates a partial cutaway view of the electronic cigarette shown in FIG. 1.

As shown in FIG. 1 and FIG. 2, according to a first embodiment of the present application, an electronic cigarette comprises a battery rod 10, an atomizer 20 and a connection structure which is provided on the junction between the battery rod 10 and the atomizer 20. The connection structure includes a first connecting piece 30 and a second connecting piece 40; by the connection of the first connecting piece 30 and the second connecting piece 40, the battery rod 10 is connected to the atomizer 20. Additionally, an airflow channel is defined in the first connecting piece 30 and/or the second connecting piece 40, and the airflow channel passes through both ends of the first connecting piece 30 and/or the second connecting piece 40, so that air flowing from the air inlet (not shown in the figures) of the side wall or the end of the electronic cigarette will flow through the airflow channel in the first connecting piece 30 and/or the second connecting piece 40, then flow into a smoke channel within the atomizer 20, and the smoke is inhaled into the mouth of the smoker.

It could be understood that, if the first connecting piece 30 is deposited at one end of the battery rod 10 and the end is closed to the atomizer 20, then the second connecting piece 40 is thereby deposited at one end of the atomizer 20 and the end is closed to the battery rod 10. By inserting the first connecting piece 30 into the second connecting piece 40 and rotating the first connecting piece 30, the first connecting piece 30 is fastened onto the second connecting piece 40, and thus the connection between the battery rod 10 and the atomizer 20 is achieved. In other embodiments, the second connecting piece 40 may be deposited at the end of the battery rod 10 and the end is closed to the atomizer 20; and the corresponding first connecting piece 30 should be deposited on the atomizer 20, so as to achieve the connection between the atomizer 20 and the battery rod 10.

Specifically in the present embodiment, the battery rod 10 is sleeved with a battery sleeve 110, and the second connecting piece 40 is deposited within the battery sleeve 110; the atomizer 20 is sleeved with an atomizer sleeve 210, and the first connecting piece 30 is deposited on the atomizer sleeve 210. By the rotation cooperation between the first connecting piece 30 and the second connecting piece 40, the connection between the battery rod 10 and the atomizer 20 is achieved, and the battery sleeve 110 and the atomizer sleeve 210 can be detachably connected to each other.

The first connecting piece 30 includes an upper electrode 330, a first insulating part 320 and a first external electrode 310, and the first insulating part 320 and the first external electrode 310 are successively sleeved on the exterior sidewall of the upper electrode 330. The first insulating part 320 is positioned between the first external electrode 310 and the upper electrode 330, so that the first external electrode 310 is electrically insulated from the upper electrode 330. Wherein the first external electrode 310 and the upper electrode 330 are made from metallic conductive material, have electrical conductivity, and are insulated from each other. A through-hole (not labeled here) for the airflow flowing though is defined in the upper electrode 330; in the present embodiment, the through-hole is the airflow channel of the first connecting piece 30.

The first external electrode 310 is substantially in the form of a hollow cylinder, and includes a main body 314 and an extension portion 316; wherein the main body 314 is sleeved within the atomizer 20; the extension portion 316 extends in the direction away from the atomizer 20 and provided outside the atomizer 20 and the main body 314 is integrated with the extension portion 316. The diameter of the extension portion 316 is less than the diameter of the main body 314, and a buckle 312 is deposited on a circumferential exterior sidewall of the extension portion 316. In the present embodiment, the buckle 312 is a bulge projecting from the circumferential exterior sidewall of the extension portion 316 in the radial direction; and the buckle 312 is deposited at edge portion of the circumferential exterior sidewall of the extension portion 316.

The second connecting piece 40 includes a lower electrode 430, a second insulating part 420 and a second external electrode 410, and the second insulating part 420 and the second external electrode are successively sleeved on the exterior sidewall of the lower electrode 430. The second insulating part 420 is positioned between the second external electrode 410 and the lower electrode 430, so that the second external electrode 410 is electrical insulated from the lower electrode 430. Wherein the second external electrode 410 and the lower electrode 430 are made from metallic conductive material, and have electrical conductivity.

Figure 3:
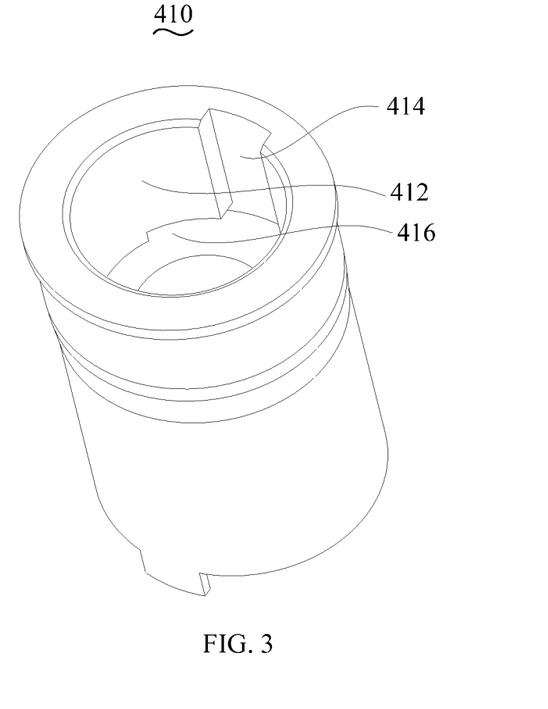
FIG. 3 illustrates a schematic view of the second external electrode shown in FIG. 1.

As shown in FIG. 3, the second external electrode 410 is substantially in form of a hollow cylinder, and the hollow cylinder on one portion of the second external electrode 410 forms a receiving hollow 412, and the portion of the second external electrode 410 is close to the atomizer 20. Moreover, both the shape and the dimension of the receiving hollow 412 match with the shape and the dimension of the extension portion 316, that is, the receiving hollow 412 is configured to contain the extension portion 316 of the first external electrode 310.

An inner wall of the receiving hollow 412 axially defines a guiding slot 414. The guiding slot 414 is configured to make the buckle 312 move downward within the guiding slot 414.

A ring-shaped projection 418 is deposited at a circumference of an inner wall of the second external electrode 410, a stop slot 416 communicating with the guiding slot 414 is circumferentially defined at an end portion of the inner wall of the receiving hollow 412 and is between the ring-shaped projection 418 and an end of the guiding slot 414, the end of the guiding slot 414 communicates with the stop slot 416, and the end wall of the guiding slot 414 and a top wall of the ring-shaped projection 418 form two sidewalls of the stop slot 416 configured for the rotation of the buckle 312.

It could be understood that the stop slot 416 may be defined at middle portion of the inner wall of the receiving hollow 412. Specifically, in the present embodiment, the second insulating part 420 is sleeved within the ring-shaped projection 418 and adhered to the inner wall of ring-shaped projection 418. The lower electrode 430 is sleeved within the second insulating part 420, and one end of the lower electrode 430 passes through the ring-shaped projection 418, that is, the end of the lower electrode 430 extends to the outside of the ring-shaped projection 418 and is close to the guiding slot 414.

The lower electrode 430 includes a hollow cylinder 434, a coaxial annular bulge 436 is deposited on an exterior sidewall of the hollow cylinder 434. The coaxial annular bulge 436 is substantially positioned in the middle portion of the cylinder 434. The coaxial annular bulge 436 abuts against a bottom wall of the ring-shaped projection 418 through the second insulating part 420 at one side of the coaxial annular bulge 436, so as to make the coaxial annular bulge 436 separate from the second external electrode 410. It could be understood that, due to the design of the coaxial annular bulge 436, the lower electrode 430 is stuck within the space formed by the ring-shaped projection 418; thereby the lower electrode 430 cannot move forward. It could be understood that, a through hole of the hollow cylinder 434 of the lower electrode 430 forms an airflow channel, and the airflow channel of the lower electrode 430 is communication with the through-hole of the upper electrode 330, which forms the airflow channel in the electronic cigarette, so that the air flowing from the lamp cap of the electronic cigarette can flow smoothly within the electronic cigarette.

The second connecting piece 40 further includes an elastomer, which is configured to make the lower electrode 430 elastically abut against the upper electrode 330 of the first connecting piece 30; and the elastomer is a spring or an elastic insulator. As shown in FIG. 2, the elastomer in the present embodiment is a spring 432, and the elastomer 432 is winded up on the hollow cylinder 434 portion at another side of the coaxial annular bulge 436. Specifically, the spring 432 winds in the axial direction along the hollow cylinder 434 and is away from the ring-shaped projection 418. Because of the elastomer, when the upper electrode 330 abuts against the lower electrode 430 and presses down the lower electrode 430, the elastomer generates certain elastic shrinkage; while the external force is relieved, the elastomer will generate the force for recovering, and generate the upward force. Preferably, the elastomer is spring 432.

When assembling the electronic cigarette according to the present embodiment, the first connecting piece 30 is aligned with the second connecting piece 40, and the first connecting piece 30 is inserted into the receiving hollow 412; then the buckle 312 moves downward along the guiding slot 414. When the buckle 312 moves to the end of the guiding slot 414, it needs to press down the first connecting piece 30, which make the upper electrode 330 and the lower electrode 430 abut against each other, the spring 432 of the lower electrode 430 elastically shrinks, and the lower electrode 430 gets a trend of moving downward. At this time, the buckle 312 reaches the stop slot 416, and be rotated into the stop slot 416, and the buckle 312 abuts against the sidewall of the stop slot 416, so that the buckle 312 is fastened in the stop slot 416, and the first connecting piece 30 can not move out from the second connecting piece 40. Besides, when the buckle 312 is fastened in the stop slot 416, the spring 432 of the lower electrode 430 produces a force for recovering the spring, that is, the lower electronic 430 generates a certain trend of moving upward, thus the lower electrode 430 closely abuts against the upper electrode 330, preventing the buckle 312 from moving out of the stop slot 416, so that the atomizer 20 is connected to the battery rod 10. After the assembly, the first external electrode 310 is electrically contacted to the second external electrode 410; the upper electrode 330 is electrically contacted to the lower electrode 430, thus the positive pole and the negative pole of the battery are respectively connected to the circuit in the electronic cigarette, which supplies power to the heating wire.

Figure 4:
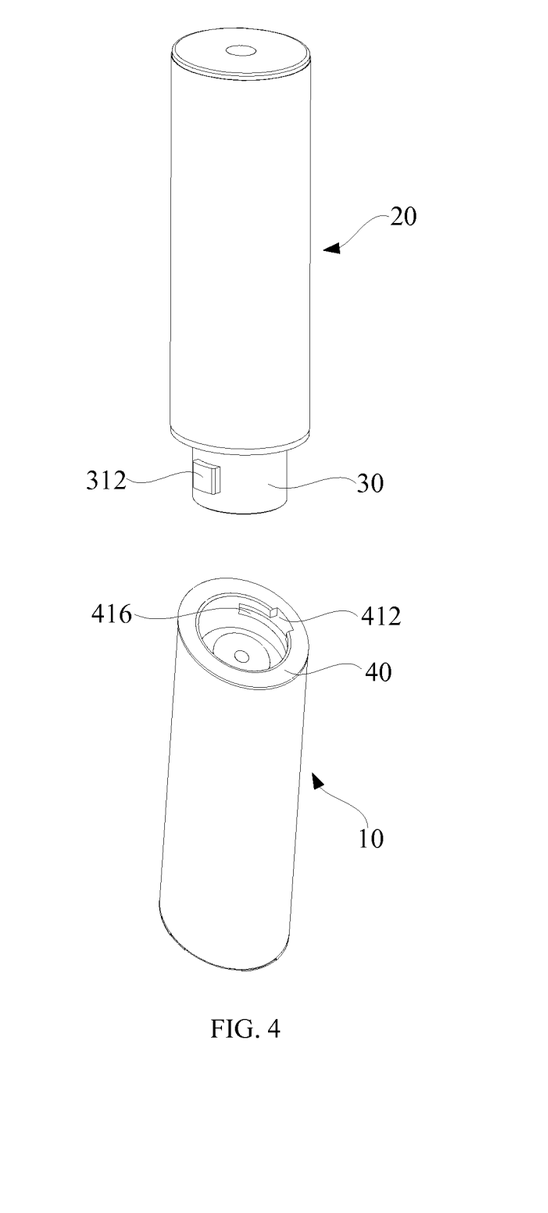
FIG. 4 illustrates a schematic view of an electronic cigarette before assembling according to a second embodiment of the present application.
Figure 5:
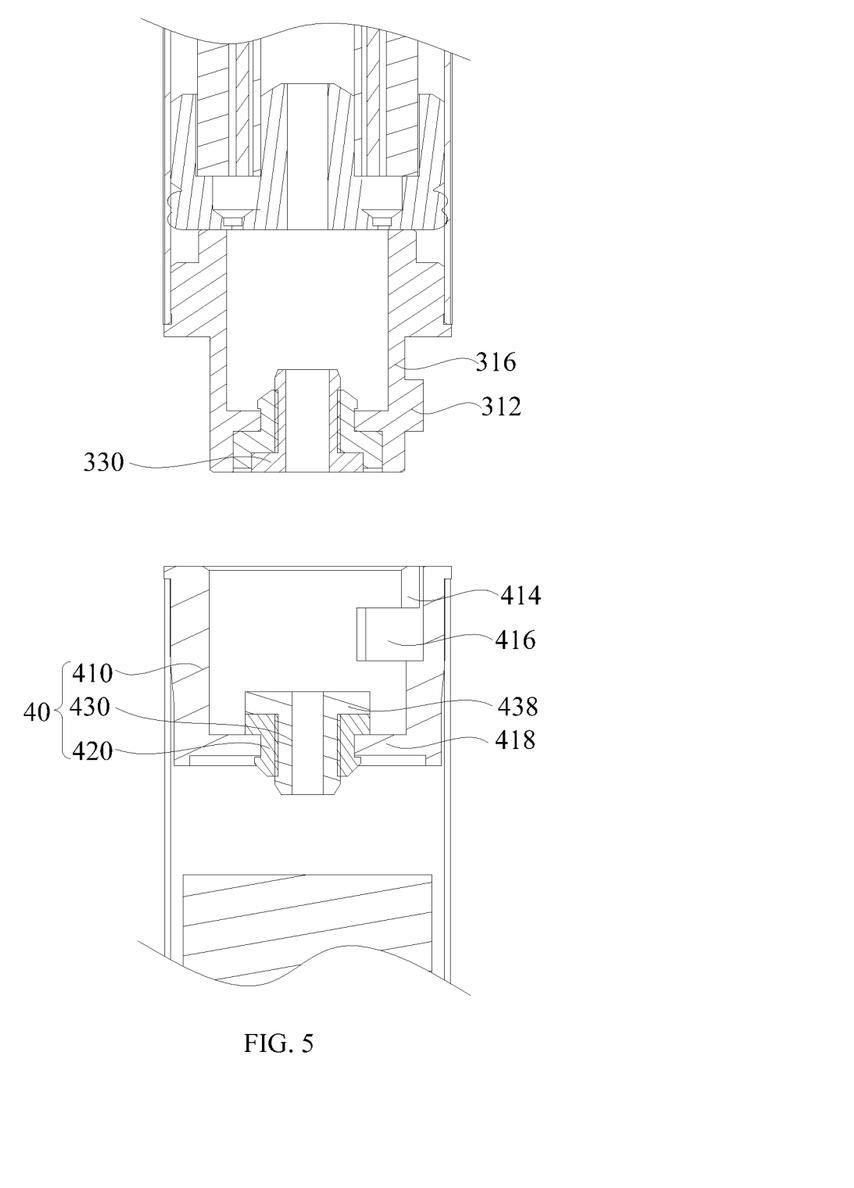
FIG. 5 illustrates a partial cutaway view of the electronic cigarette shown in FIG. 4.

As shown in FIG. 4 and FIG. 5, in the electronic cigarette according to the second embodiment of the present application, the buckle 312 is deposited in a middle portion of the circumferential exterior sidewall of the extension portion. It could be understood that, in other embodiments, the buckle 312 may be deposited in any portion of the circumferential exterior sidewall of the extension portion 316.

Figure 6:
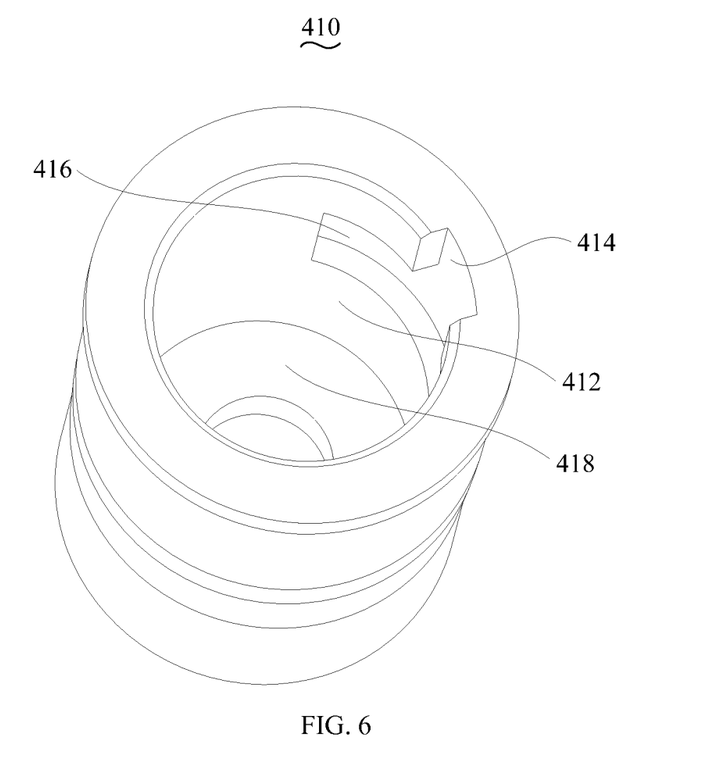
FIG. 6 illustrates a schematic view of the second external electrode shown in FIG. 4.

As shown in FIG. 6, the stop slot 416 according to the present embodiment is circumferentially formed at a middle portion of the inner wall of the receiving hollow 412, and the stop slot 416 is in communication with the guiding slot 414. In specific, the stop slot 416 is perpendicular to the guiding slot 414.

As shown in FIG. 5, the lower electrode 430 is substantially in form of T, that is, a flange 438 is provided on one end of the lower electrode 430, and the flange 438 abuts against the top wall of the ring-shaped projection 418 through the second insulating part 420.

The second insulating part 420 according to the present embodiment is made from soft material. The soft material is at least one kind from polyurethane rubber, silicone rubber and polystyrene. When suffering the extrusion from the external force, the second insulating part 420 can generate certain elastic deformation. That is to say, the second insulating part 420 here is an elastomer.

According to the electronic cigarette of the present embodiment, when the first connecting piece 30 is inserted into the receiving hollow 412, and the buckle 312 moves downward along the guiding slot 414 until to the end of the guiding slot 414, the upper electrode 330 and the lower electrode 430 abut against each other. At this time, the upper electrode 330 is pushed down with a little force so that the upper electrode 330 extrudes the lower electrode 430, thus the second insulating part 420 which flexibly abuts against the lower electrode 430 will generate elastic deformation. Thereby, the buckle 312 reaches the stop slot 416, and is rotated into the stop slot 416. Additionally, the buckle 312 abuts against the sidewall of the stop slot 416, which make the buckle 312 fastened in the stop slot 416, so that the atomizer 20 is permanent connected to the battery rod 10. Besides, when the buckle 312 is fastened in the stop slot 416, the second insulating part 420 will produce a force for recovering, that is, the second insulating part 420 will generate a certain trend of moving upward, thus the upper electrode 330 closely abuts against the lower electrode 430, preventing the buckle 312 from moving out of the stop slot 416.

According to the electronic cigarette of the present embodiment, by mounting the buckle 312 on the first connecting piece 30, firstly the first connecting piece 30 is inserted into the receiving hollow 412 and makes the buckle 312 move downward along the guiding slot 414. When the buckle 312 moves to the end of the guiding slot 414, the lower electrode 430 is pressed down which makes the buckle 312 reaches the stop slot 416. Then the buckle 312 is rotated thus the buckle 312 enters into the stop slot 416, so that the first connecting piece 30 is connected to the second connecting piece 40. Furthermore, when the buckle 312 is limited in the stop slot 416, the upper electrode 330 elastically abuts against the lower electrode 430, preventing the buckle 312 from slipping out of the stop slot 416, and the problem of the atomizer 20 falling off from the inside of the battery rod 10 is avoid. Additionally, the electrical connection in the present application is relatively well, and the mechanical strength is high, which make it not easy to break. Only one buckle is provided, and the construction is simple; it is convenient for the manufacture and it is cost-effective; the assembly method is more convenient and simple. Besides, the battery rod 10 is easier to align with the atomizer 20, and the user experience is improved.

Although the present application is illustrated with the embodiments accompanying the drawings, the present application is not limited to the above-mentioned specific embodiments, and the above-mentioned embodiments are only for illustration, not for limitation. In the inspiration of the present application, those skilled in the art may make many modifications, without going beyond the purpose and the scope the claims intend to protect of the present application; all these belong to the protection of the present application.

What is claimed is:

1. An electronic cigarette comprising a battery rod, an atomizer and a connection structure provided on a junction between the battery rod and the atomizer, wherein the connection structure includes a first connecting piece and a second connecting piece;

a buckle projects radially from an exterior sidewall of the first connecting piece;

a receiving hollow, a guiding slot and a stop slot are defined in the second connecting piece; the receiving hollow is configured to hold the first connecting piece inserted; the guiding slot matching with the buckle is axially formed on an inner wall of the receiving hollow; the stop slot is in communication with the guiding slot;

wherein the first connecting piece comprises an upper electrode, a first insulating part and a first external electrode, the upper electrode abuts against the second connecting piece; the first insulating part and the first external electrode are successively sleeved on an exterior sidewall of the upper electrode; and the first insulating part is configured to make the first external electrode electrically insulated from the upper electrode;

wherein the first external electrode includes a main body and an extension portion; the main body is defined in the atomizer, and the extension portion extends in a direction opposite to the atomizer; the buckle is defined on an edge portion of a circumferential exterior sidewall of the extension portion;

wherein the second connecting piece comprises a lower electrode, an elastomer, a second insulating part and a second external electrode; the elastomer is configured to make the lower electrode elastically abut against the upper electrode; the second insulating part and the second external electrode are successively sleeved on an exterior sidewall of the lower electrode; the second insulating part is configured to make the second external electrode electrically insulated from the lower electrode; the elastomer is a spring or an elastic insulating part; the second insulating part is made from soft material; the soft material is at least one kind from polyurethane rubber, silicone rubber and polystyrene;

wherein the second external electrode is substantially in form of a hollow cylinder, the receiving hollow is defined on one portion of the second external electrode, and the portion is close to the atomizer; a ring-shaped projection is defined at a circumference of an inner wall of the second external electrode, and one end of the lower electrode passes through the ring-shaped projection, the end is close to the guiding slot the stop slot is circumferentially defined at an end portion of the inner wall of the receiving hollow and is between the ring-shaped projection and an end of the guiding slot, the end of the guiding slot communicates with the stop slot, and the end wall of the guiding slot and a top wall of the ring-shaped projection form two sidewalls of the stop slot configured for the rotation of the buckle;

wherein the lower electrode includes a hollow cylinder, and a coaxial annular bulge is defined on an exterior sidewall of the hollow cylinder; the coaxial annular bulge abuts against a bottom wall of the ring-shaped projection through the second insulating part at one side of the coaxial annular bulge, and a through hole of the hollow cylinder of the lower electrode forms an airflow channel; a flange is provided on one end of the lower electrode, the flange abuts against the top wall of the ring-shaped projection through the second insulating part;

wherein the elastomer is winded up on the hollow cylinder portion at another side of the coaxial annular bulge; when the upper electrode abuts against the lower electrode and presses down the lower electrode, the elastomer shrinks elastically to make the buckle enter into the stop slot;

wherein end surfaces of the first external electrode, the first insulating part and the upper electrode which are close to the battery assembly are on a same plane, a diameter of a cross section of an end of the lower electrode which is close to the battery assembly is larger than or equal to a diameter of a cross section of a hollow part of the upper electrode, and is smaller or equal to a diameter of a cross section of an end of the upper electrode which is close to the battery assembly;

a diameter of a cross section of an end of the second insulating part which is close to the atomization assembly is larger than the diameter of the cross section of the end of the upper electrode which is close to the battery assembly; and when assembling the electronic cigarette, inserting the first connecting piece into the receiving hollow and moving it downward along the guiding slot until the buckle reaches the stop slot and having the first connecting piece press down the lower electrode, then rotating the first connecting piece so that the buckle enters into the stop slot and is locked.

2. The electronic cigarette according to claim 1, wherein the airflow channel is defined in the first connecting piece and/or the second connecting piece, and the airflow channel passes through both ends of the first connecting piece and/or the second connecting piece.

* * * * *